(12) United States Patent
Sandwick

(10) Patent No.: US 8,827,696 B1
(45) Date of Patent: Sep. 9, 2014

(54) CAST ORTHODONTIC RETAINER SYSTEM

(76) Inventor: Todd W. Sandwick, Fosston, MN (US)

(*) Notice: Subject to any disclaimer, the term of this patent is extended or adjusted under 35 U.S.C. 154(b) by 328 days.

(21) Appl. No.: 12/904,528

(22) Filed: Oct. 14, 2010

(51) Int. Cl.
*A61C 3/00* (2006.01)

(52) U.S. Cl.
USPC .............................................. 433/6

(58) Field of Classification Search
USPC ............... 433/6–7, 10–11, 17–21, 24, 34, 433/214–215, 167–183, 191–194, 199.1, 433/200.13; 264/16–20; 29/896.1, 896.11
See application file for complete search history.

(56) References Cited

U.S. PATENT DOCUMENTS

| | | | | |
|---|---|---|---|---|
| 4,526,539 A | * | 7/1985 | Blechman et al. | 433/18 |
| 4,562,882 A | * | 1/1986 | Alleluia | 164/529 |
| 4,755,139 A | * | 7/1988 | Abbatte et al. | 433/6 |
| 5,059,118 A | * | 10/1991 | Breads et al. | 433/6 |
| 5,267,862 A | * | 12/1993 | Parker | 433/215 |
| 5,944,526 A | * | 8/1999 | Liu | 433/176 |
| 2004/0137408 A1 | * | 7/2004 | Embert et al. | 433/201.1 |
| 2008/0057457 A1 | * | 3/2008 | Inman | 433/6 |

* cited by examiner

*Primary Examiner* — Yogesh Patel
(74) *Attorney, Agent, or Firm* — Jason L. Gilbert

(57) ABSTRACT

A cast orthodontic retainer system for reducing discomfort and improving durability. The cast orthodontic retainer system generally includes a palatal portion for positioning against the palate of a patient's mouth and a retention portion for extending across an anterior portion of the patient's teeth. The palatal portion of the present invention is fabricated of a cast metallic material, thus allowing for the palatal portion to be substantially thinner than the palatal portions of retainers in the prior art. In a preferred embodiment, the palatal portion of the present invention will be fabricated of a combination of cobalt, chromium and molybdenum (generally marketed under the trademark VITALLIUM). The palatal portion of the orthodontic retainer is preferably cast from the metallic material utilizing the "lost wax" technique of casting.

3 Claims, 13 Drawing Sheets

CAST ORTHODONTIC RETAINER SYSTEM

CROSS REFERENCE TO RELATED APPLICATIONS

Not applicable to this application.

STATEMENT REGARDING FEDERALLY SPONSORED RESEARCH OR DEVELOPMENT

Not applicable to this application.

BACKGROUND OF THE INVENTION

1. Field of the Invention

The present invention relates generally to an orthodontic retainer and more specifically it relates to a cast orthodontic retainer system which includes a thin palatal portion cast from a metallic material for improving the comfort of a patient utilizing an orthodontic retainer.

2. Description of the Related Art

Any discussion of the related art throughout the specification should in no way be considered as an admission that such related art is widely known or forms part of common general knowledge in the field.

Orthodontic retainers have been in use for years in the orthodontic field for providing orthodontic retention after completion of an active phase of orthodontic treatment. The most commonly utilized orthodontic retainer appears to be the Hawley-type retainer design, which is generally comprised of a palatal portion and an arch wire attached at both ends to the palatal portion. The palatal portion is generally positioned against the palate of a patient and the arch wire generally extends around the anterior surface of the frontal teeth of a patient.

The palatal portion of previously-used orthodontic retainers is generally comprised of a plastic or acrylic material. However, the use of such materials for the palatal portion of orthodontic retainers generally suffers from a number of shortcomings. The palatal portion is generally bulky. The acrylic and plastic materials utilized for such palatal portions will generally require a minimum thickness of 1.5 millimeters or more to provide the requisite structural strength, thus resulting in discomfort for a patient who must wear such a retainer for hours each day. Further, the acrylic or plastic material utilized for the palatal portion of previously-existing retainers often breaks easily, requiring costly repairs or replacement of the orthodontic retainer.

Because of the inherent problems with the related art, there is a need for a new and improved cast orthodontic retainer system which includes a thin palatal portion cast from a metallic material for improving the comfort of a patient utilizing an orthodontic retainer.

BRIEF SUMMARY OF THE INVENTION

The invention generally relates to an orthodontic retainer which includes a thin palatal portion cast from a metallic material and a method for fabricating the same. The retainer is generally comprised of a palatal portion for positioning against the palate of a patient's mouth and a retention portion for extending across an anterior portion of the patient's teeth. The palatal portion of the present invention is comprised of a cast metallic material, thus allowing for the palatal portion to be substantially thinner than the palatal portions of retainers in the prior art. In a preferred embodiment, the palatal portion of the present invention will be comprised of a metal alloy comprised of carbon, silicon, manganese, cobalt, chromium and molybdenum (generally marketed under the trademark VITALLIUM by Howmedica, Inc.). The palatal portion of the orthodontic retainer is preferably cast from the metallic material utilizing the "lost wax" technique of casting.

There has thus been outlined, rather broadly, some of the features of the invention in order that the detailed description thereof may be better understood, and in order that the present contribution to the art may be better appreciated. There are additional features of the invention that will be described hereinafter and that will form the subject matter of the claims appended hereto. In this respect, before explaining at least one embodiment of the invention in detail, it is to be understood that the invention is not limited in its application to the details of construction or to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

Figure 1:
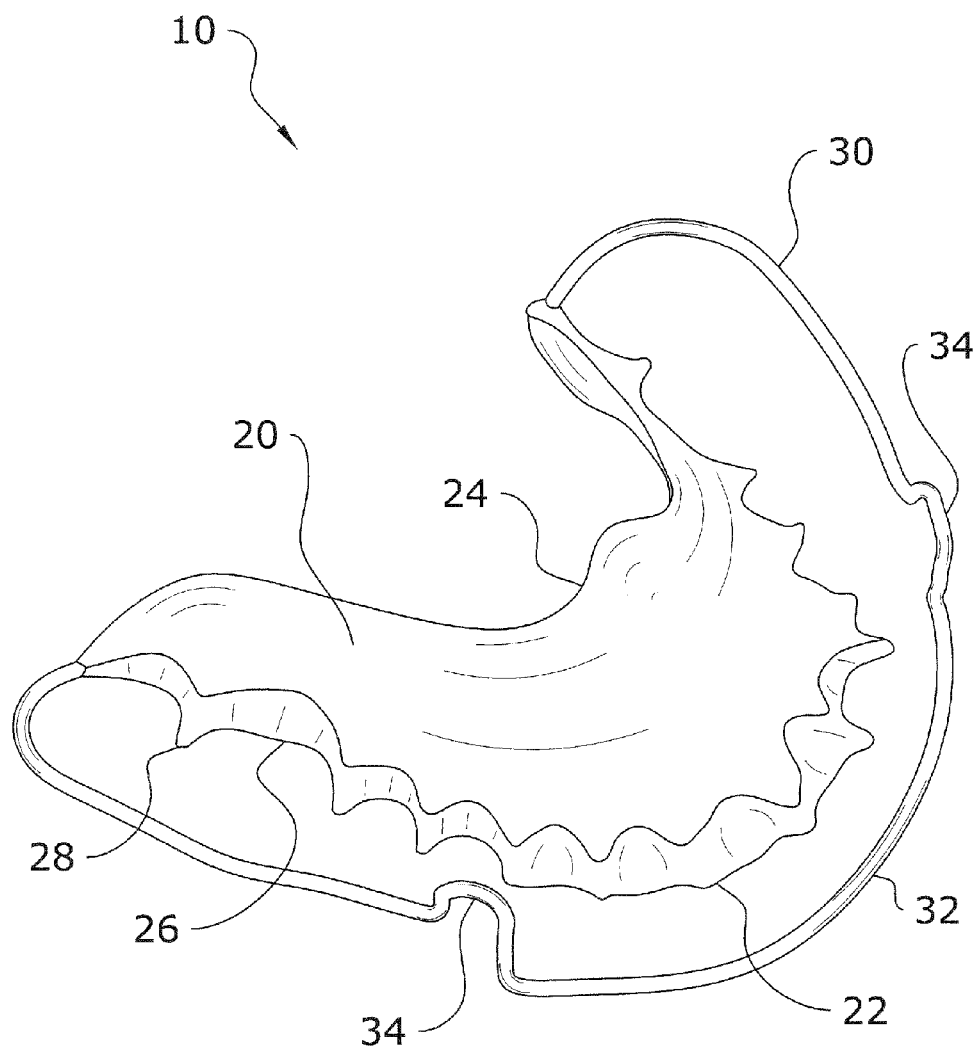
FIG. 1 is an upper perspective view of the present invention.

A. Overview.

Turning now descriptively to the drawings, in which similar reference characters denote similar elements throughout the several views, FIGS. 1 through 7 illustrate a removable cast orthodontic retainer system 10, which comprises a palatal portion 20 for positioning against the palate of a patient's mouth and a retention portion 30 for extending across an anterior portion of the patient's teeth 12. The palatal portion 20 of the present invention is comprised of a cast metallic material, thus allowing for the palatal portion 20 to be substantially thinner than the palatal portions 20 of retainers in the prior art. In a preferred embodiment, the palatal portion 20 of the present invention will be comprised of a combination of cobalt, chromium and molybdenum (generally marketed under the trademark VITALLIUM by Howmedica, Inc.). The palatal portion 20 of the orthodontic retainer 10 is preferably cast from the metallic material utilizing the "lost wax" technique of casting.

B. Palatal Portion.

As shown in FIG. 1, the cast orthodontic retainer system 10 includes a palatal portion 20, which will generally be positioned against the palate of a patient's mouth when the present invention is in use. The palatal portion 20 is preferably custom fit to the palate of a particular patient and will generally be comprised of a substantially plate-like member which includes a front edge 22 and a rear edge 24.

Figure 2:
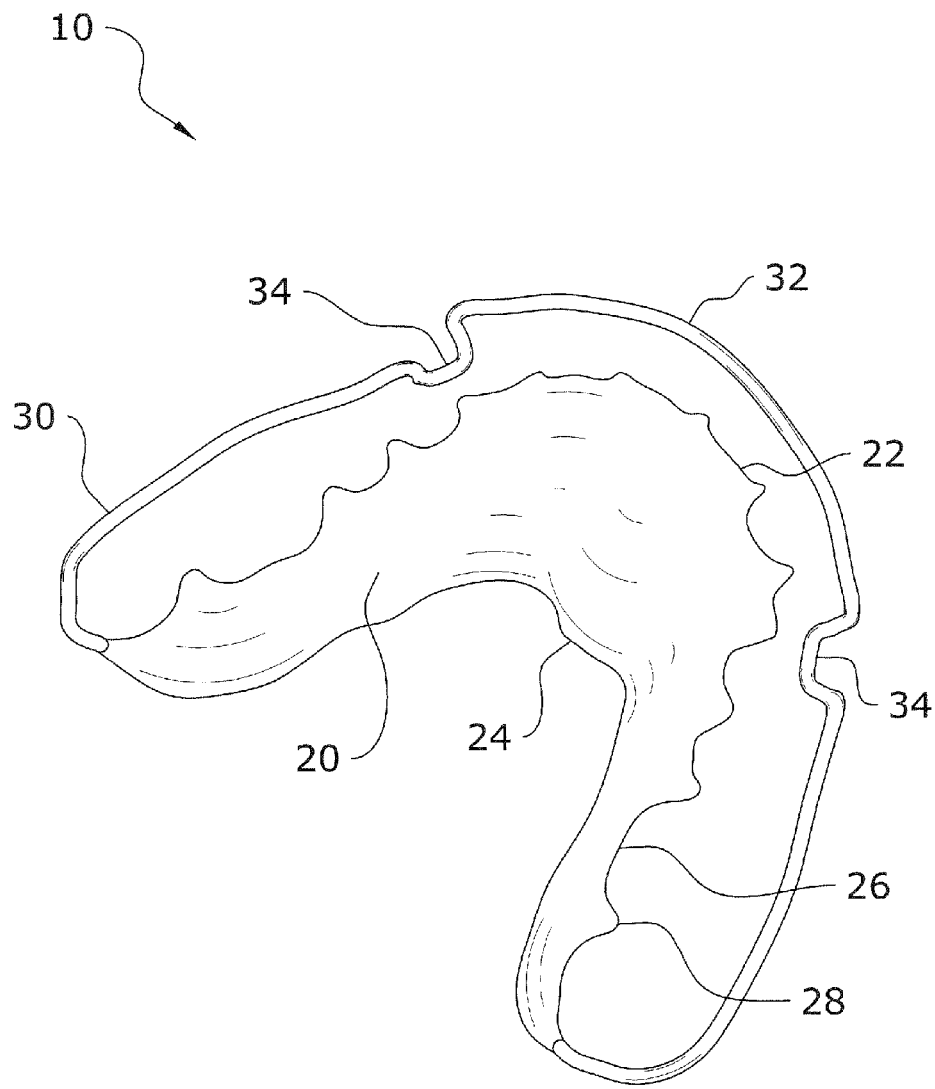
FIG. 2 is a lower perspective view of the present invention.
Figure 4:
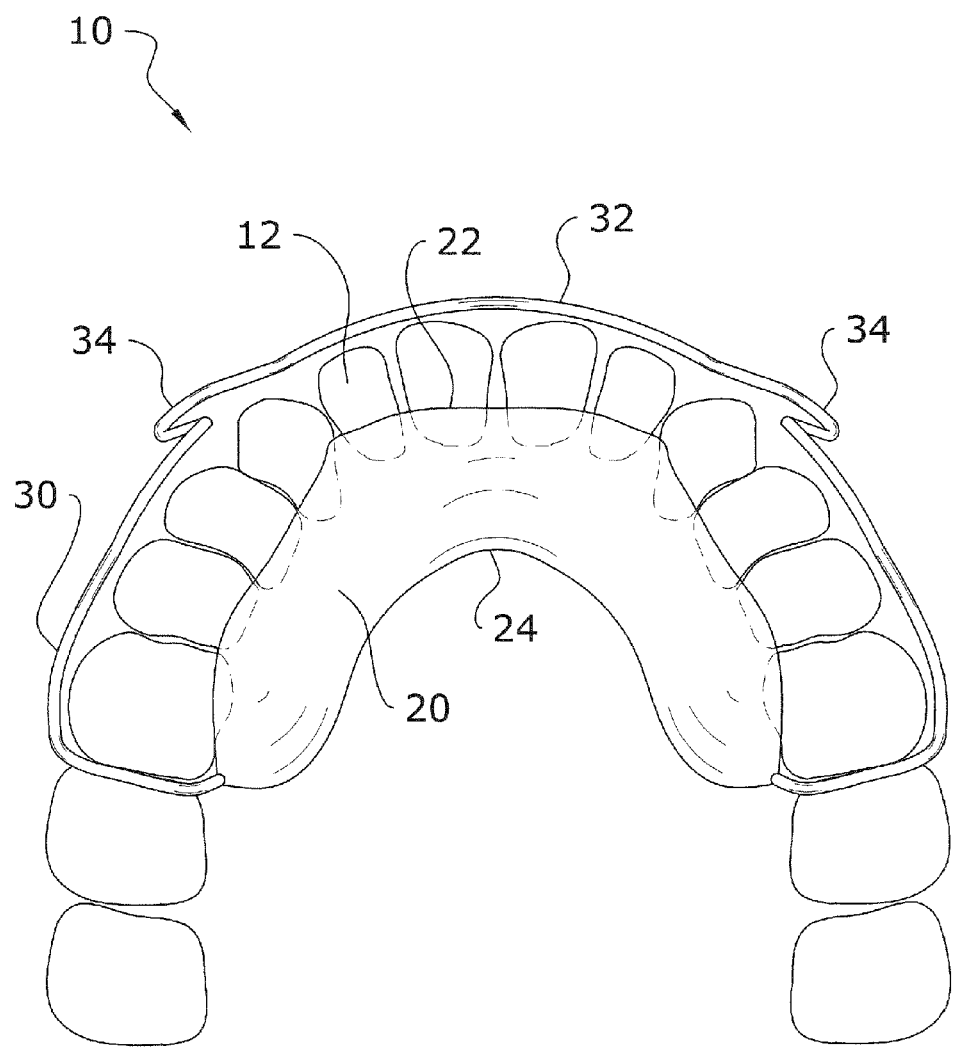
FIG. 4 is a lower view of the present invention in use.

The front edge 22 of the palatal portion 20 of the cast orthodontic retainer system 10 will generally be positionable adjacent the lingual surfaces of a patient's anterior teeth 12. The palatal portion 20 will generally extend rearwardly along the lingual surfaces of at least a portion of the patient's posterior teeth as shown in FIG. 4. The rear edge 24 of the palatal portion 24 may be curved as shown in FIG. 2 or, in some embodiments, may be comprised of a straight edge.

Figure 3:
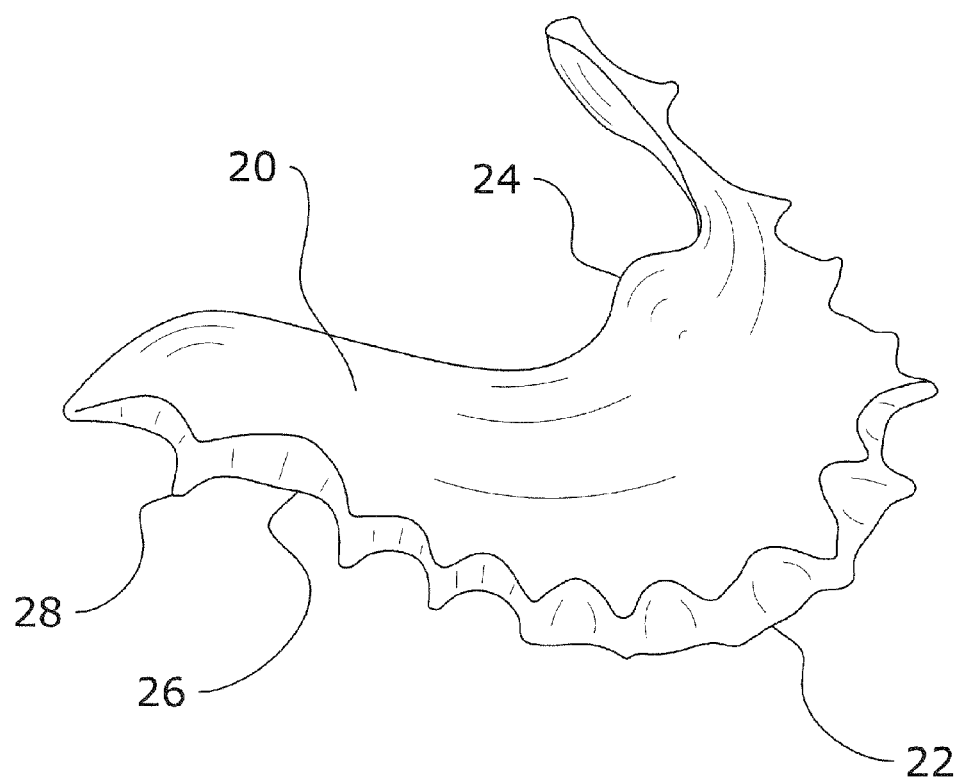
FIG. 3 is an upper perspective view of the palatal portion of the present invention.

As shown in FIG. 3, the front edge 22 of the palatal portion 20 of the cast orthodontic retainer system 10 will generally include a plurality of indentations 26 and projections 28. The indentations 26 will generally be sized and shaped to receive a rear surface of the patient's teeth. As such, the indentations 26 will generally be preformed to accommodate the layout of teeth of a particular patient. The projections 28 will generally extend at least partially between the teeth of the patient and will similarly be preformed to accommodate the particular layout of teeth of a particular patient.

The palatal portion 20 of the present invention will generally be cast from a metallic material using a process such as but not limited to lost-wax casting. The palatal portion 20 is preferably comprised of a thickness no greater than 0.30 millimeters. While various types of metallic materials may be utilized for the palatal portion 20, the metallic material is preferably comprised of a metal alloy. VITALLIUM is a brand of metal alloy that is suitable for use within the present invention. VITALLIUM is believed to be comprised of carbon, silicon, manganese, cobalt, chromium and molybdenum. However, it should be appreciated that various other types of metals and/or metal alloys may be utilized in fabricating the palatal portion 20 of the present invention so long as the material used provides the requisite durability and strength at thicknesses of less than 0.30 millimeters.

C. Retention Portion.

As shown in FIG. 4, the cast orthodontic retainer system 10 will generally include a retention portion 30 extending across the front edge 22 of the palatal portion 20. The retention portion 30 will be configured to extend across an anterior portion of a patient's teeth 12 so as to ensure proper alignment and setting of the teeth 12 after completion of orthodontic work.

The retention portion 30 of the present invention is preferably comprised of a labial wire 32 which is attached at both ends to the palatal portion 20 of the cast orthodontic retainer system 10. The labial wire 32 will generally be welded to the palatal portion 20 in a manner which retains the teeth 12 of a patient between the labial wire 32 and the front edge 22 of the palatal portion 20. The labial wire 32 generally extends outwardly from rear points on the front edge 22 of the palatal portion 20 through spaces between molars and cuspids and extends around the cuspids to extend tightly around the anterior portion of the patient's front teeth 12 or incisors. The labial wire 32 will also generally include at least one arch wire 34 portion extending upwardly as shown in FIG. 4 for gripping by the patient.

Figure 5:
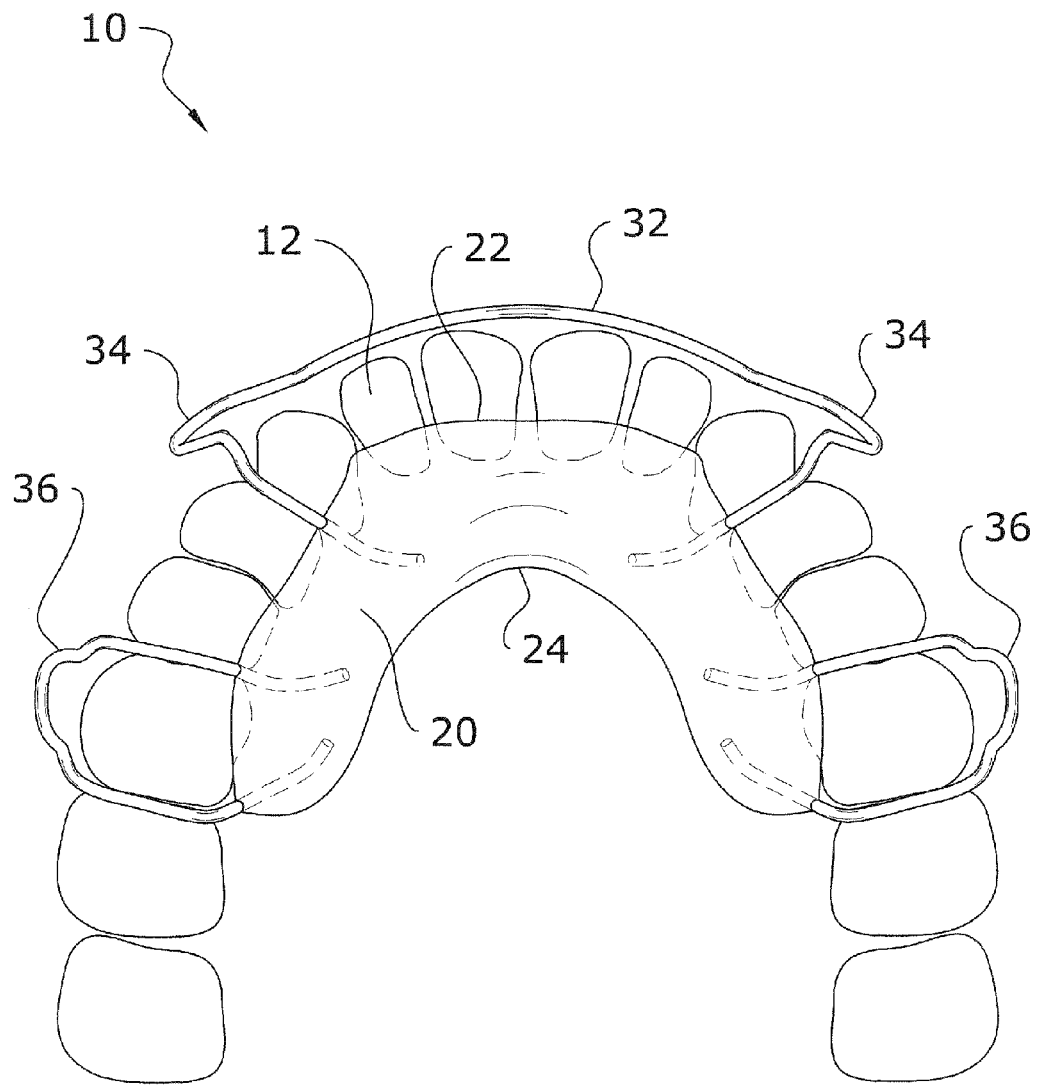
FIG. 5 is a lower view of a second embodiment of the present invention in use.
Figure 6:
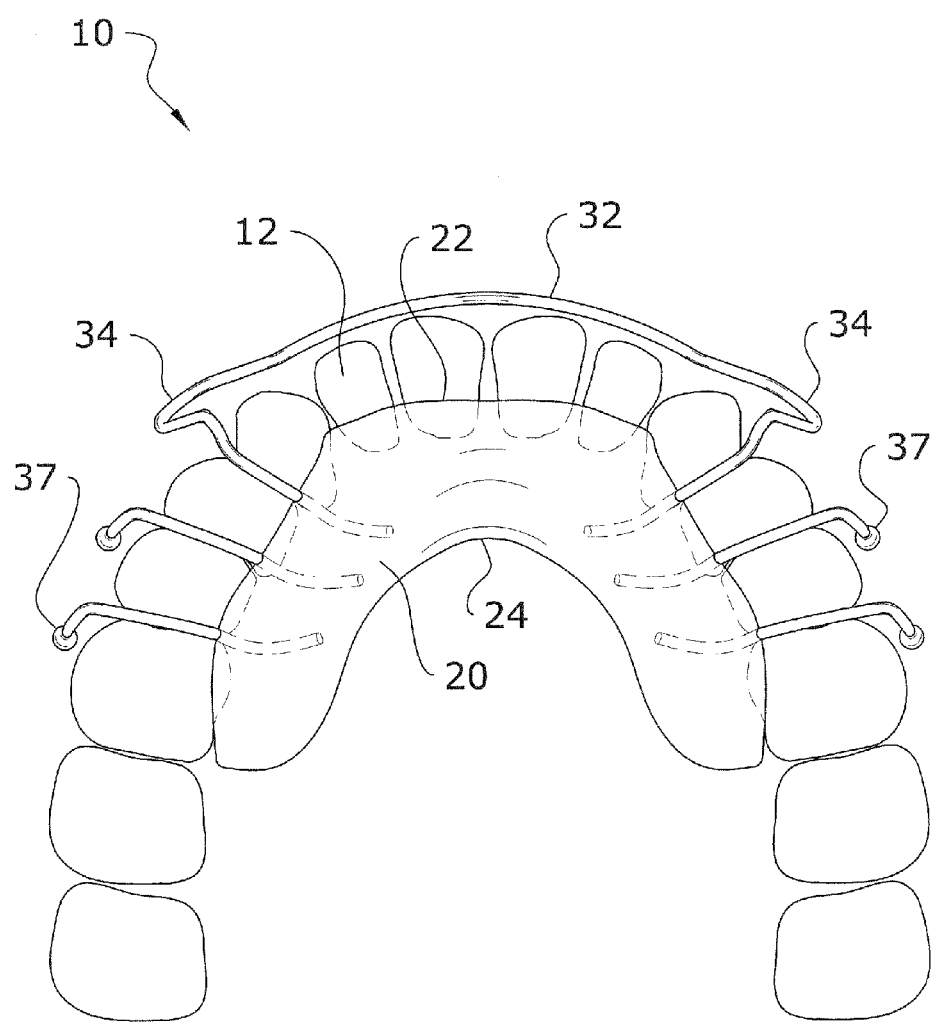
FIG. 6 is a lower view of a third embodiment of the present invention in use.
Figure 7:
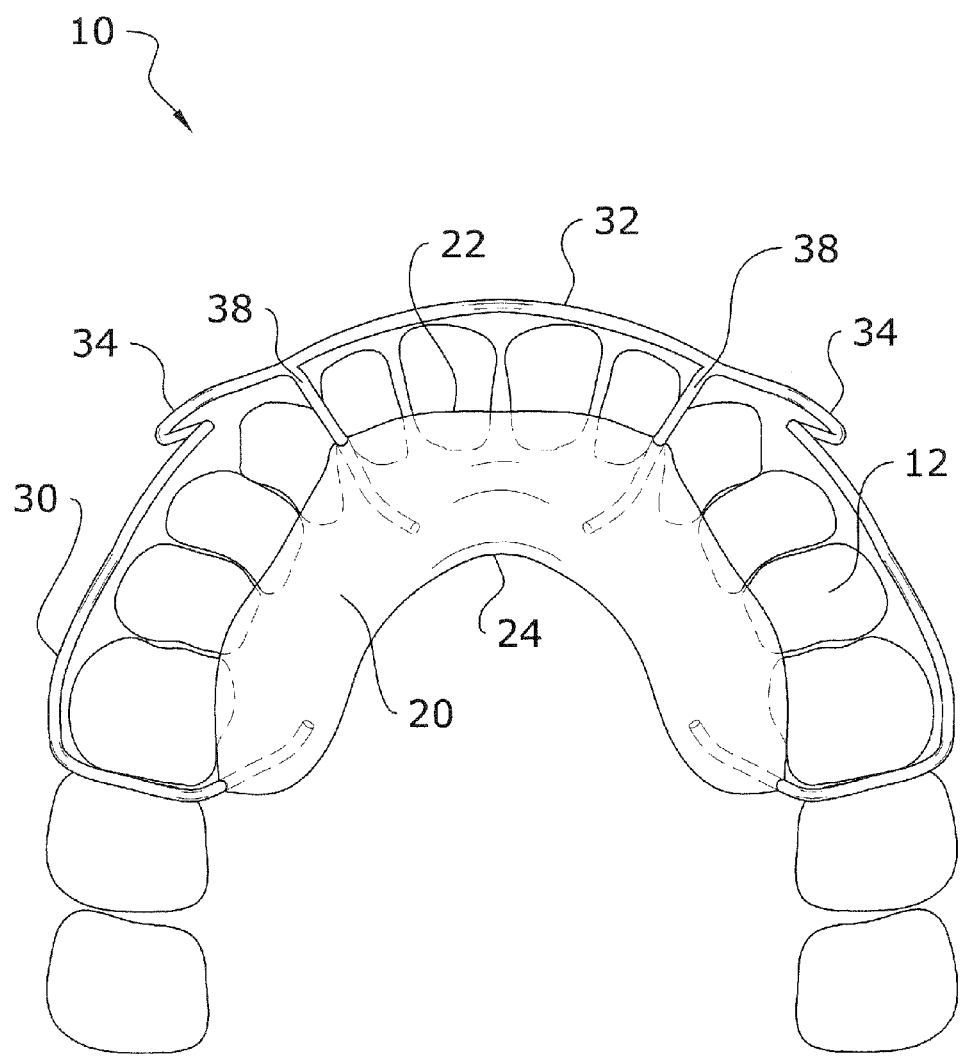
FIG. 7 is a lower view of a fourth embodiment of the present invention in use.

FIGS. 5 through 7 illustrate various alternate configurations of the retention portion 30 of the present invention for accommodating various different orthodontic retention applications. As shown in FIG. 5, the retention portion 30 of the present invention may include an Adams clasp 36 which utilizes the buccomesial and distoproximal undercuts of a tooth for retention. The Adams clasp 36 will generally be comprised of a U-shaped clasp which is attached directly to the palatal portion 20 of the present invention. The U-shaped portion of the Adams clasp 36 will generally extend between teeth 12 forwardly around an anterior portion of a tooth.

As shown in FIG. 6, the retention portion 30 of the present invention may also include one or more ball clasps 37. Each ball clasp 37 will generally be attached at its rear end to the palatal portion 20 of the cast orthodontic retainer system 10 and extend forwardly between teeth 12 such as cuspids. A first ball clasp 37 will generally extend along a first side of a tooth 12 such as a cuspid and a second ball clasp 37 will generally extend along a second side of the tooth 12 for ensuring proper retention and alignment.

As shown in FIG. 7, the retention portion 30 of the present invention may also include one or more stabilizing wires 38. The stabilizing wires 38 will generally be attached at a first end to the palatal portion 20 of the present invention and at a second end to a point on the labial wire 32 of the retention portion 30 such that each stabilizing wire 38 extends across the teeth 12 of the patient. The stabilizing wires 38 of the present invention provide additional stability for the present invention as a whole and inadvertent movement or other actions which may compromise the alignment and retention functions of the present invention as a whole.

D. Preferred Method of Fabrication of the Present Invention.

FIGS. 8 through 13 illustrate a preferred method of fabricating the palatal portion of the orthodontic retainer utilizing the lost wax technique of casting. While the figures show various embodiments of a Hawley-type retainer, it is appreciated that the methods of fabrication described herein are not necessarily limited to Hawley-type retainers and may be utilized in constructing various other designs of orthodontic retainer devices.

Figure 8:
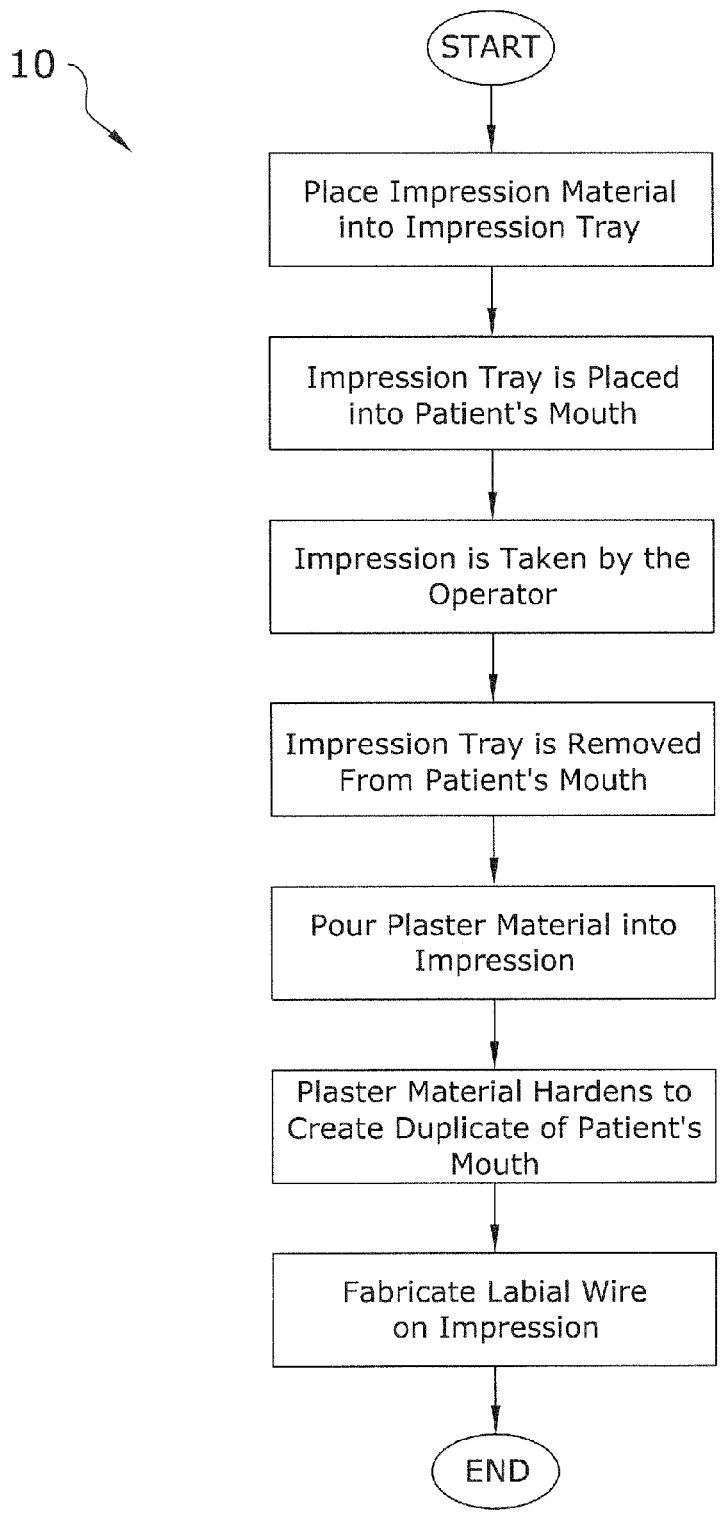
FIG. 8 is a flowchart illustrating the process of creating a duplicate of a patient's mouth during the fabrication of the present invention.

As illustrated in FIG. 8, a duplicate of a patient's mouth is created by utilizing impression material. An impression tray is first filled with an impression material and placed within a patient's mouth to obtain an impression of the patient's upper mouth and teeth. Various types of impression material may be utilized, including but not limited to alginate, polyvinyl, reversible hydrocolloid or polyether impression materials. After removing the impression tray from the patient's mouth, a plaster material will be poured into the impression and allowed to harden to create a duplicate of a patient's mouth and teeth 12. The labial wire 32 may then be sized to fit the duplicate of the patient's teeth 12.

Figure 9:
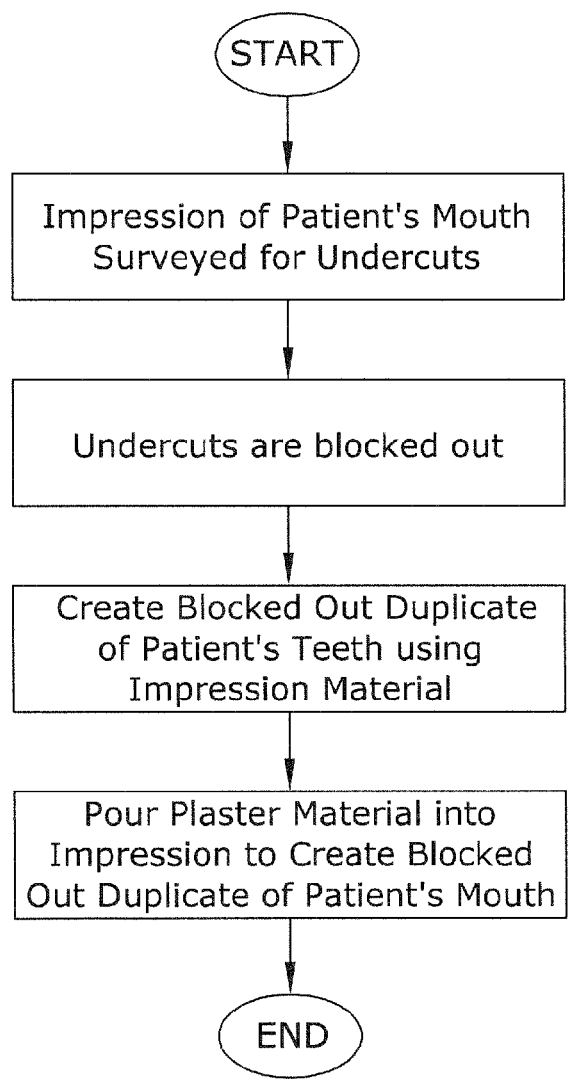
FIG. 9 is a flowchart illustrating the process of creating a blocked out duplicate of a patient's teeth during the fabrication of the present invention.

As illustrated in FIG. 9, the resulting duplicate is then surveyed for undercuts. Undesired undercuts are then at least partially blocked out using wax or a similar substance so as to ensure proper spacing between the palatal portion 20 of the orthodontic retainer 10 and the patient's teeth 12 after casting. Failure to properly block out undercuts may result in the retainer 10 becoming "locked in" to the teeth 12 of a patient. The duplicate is then pressed into impression material and the resulting blocked out impression is filled with a plaster material to create a blocked out duplicate of a patient's mouth and upper teeth.

Figure 10:
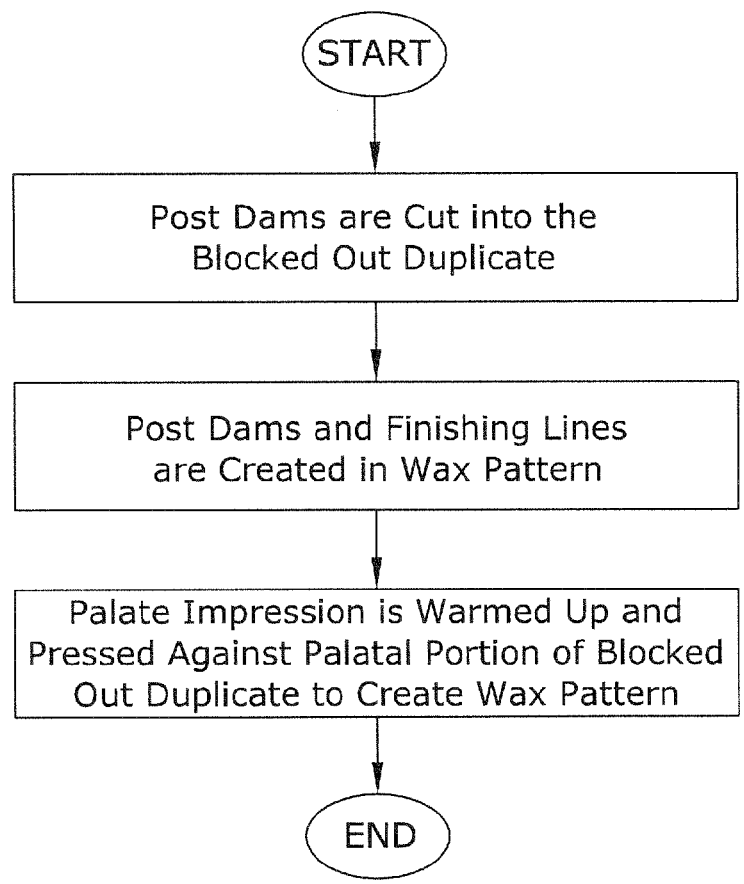
FIG. 10 is a flowchart illustrating the process of creating a palatal impression of a patient's palate during the fabrication of the present invention.

As illustrated in FIG. 10, post dams may then be cut into the blocked out duplicate to ensure a complete seal between the palatal portion of the retainer and a patient's mouth when the completed cast orthodontic retainer system 10 is used. After the blocked out duplicate of a patient's mouth is completed and post dams have been cut, a sheet of malleable material will generally be warmed up and pressed against the palatal portion of the blocked out duplicate so as to duplicate the surface texture and grooves of the patient's palate to the malleable material. Preferably the malleable material will be comprised of wax. However, it is appreciated that various other materials may be utilized so long as they are capable of both retaining the surface texture of the palate and melting upon application of heat. After applying the sheet to the palate, a palatal impression will be obtained which will duplicate the surface texture, shape and grooves of the patient's palate for casting. Post dams and finishing lines may then be created in the palatal impression.

Figure 11:
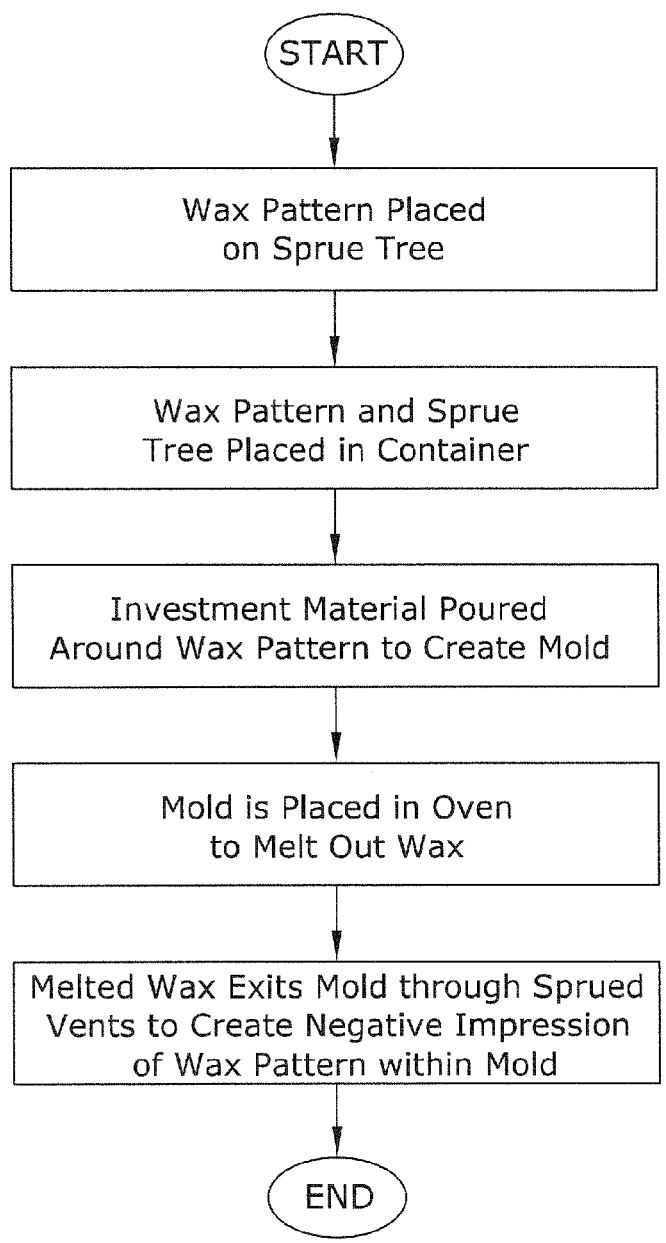
FIG. 11 is a flowchart illustrating the "lost wax" process utilized during the fabrication of the present invention.
Figure 12:
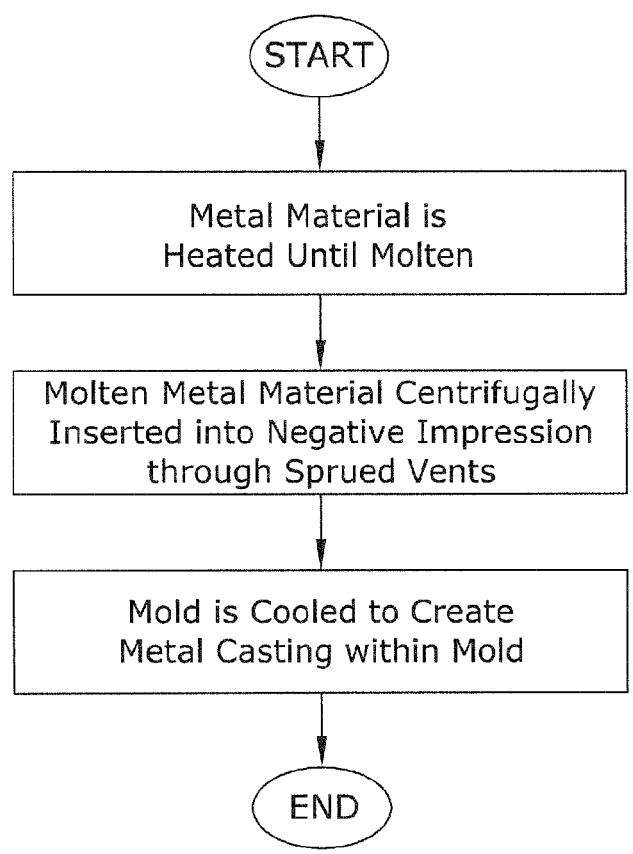
FIG. 12 is a flowchart illustrating the metal casting process utilized during the fabrication of the present invention.

After duplication of the patient's palate into a palatal impression and the inclusion of post dams and finishing lines, lost wax casting may be applied to the palatal impression to fabricate the finished palatal portion of the cast orthodontic retainer system 10. FIGS. 11 and 12 illustrate the overall process of lost wax casting. First, the palatal impression will be placed on a sprue tree, which is generally comprised of a tree-like structure of wax or another malleable material which will assist in creation of vents through which the melted malleable material may exit the mold after it has been created and heated up. The palatal impression and attached sprue tree are then placed into a container and surrounded by an investment material such as plaster to create a mold. The mold is then placed in an oven or other heating device and heated to the point that the palatal impression and sprue tree both melt. The melting of the sprue tree creates vents through which the melted palatal impression may exit the mold, thus creating a negative impression of the palatal impression within the mold.

As illustrated in FIG. 12, a metal material is then obtained and heated until molten. As described previously, various types of metal materials may be utilized for the present invention, though it is preferable to utilize a metal alloy comprised of cobalt, chromium and molybdenum. The molten metal material is inserted into the negative palatal impression within the mold. In a preferred embodiment, the molten material will be inserted into the negative impression through centrifugal force utilizing a centrifuge. After the negative impression has been sufficiently filled with molten metal material, the mold is removed from heat and allowed to cool, thus hardening the molten metal material within the negative impression of the mold.

Figure 13:
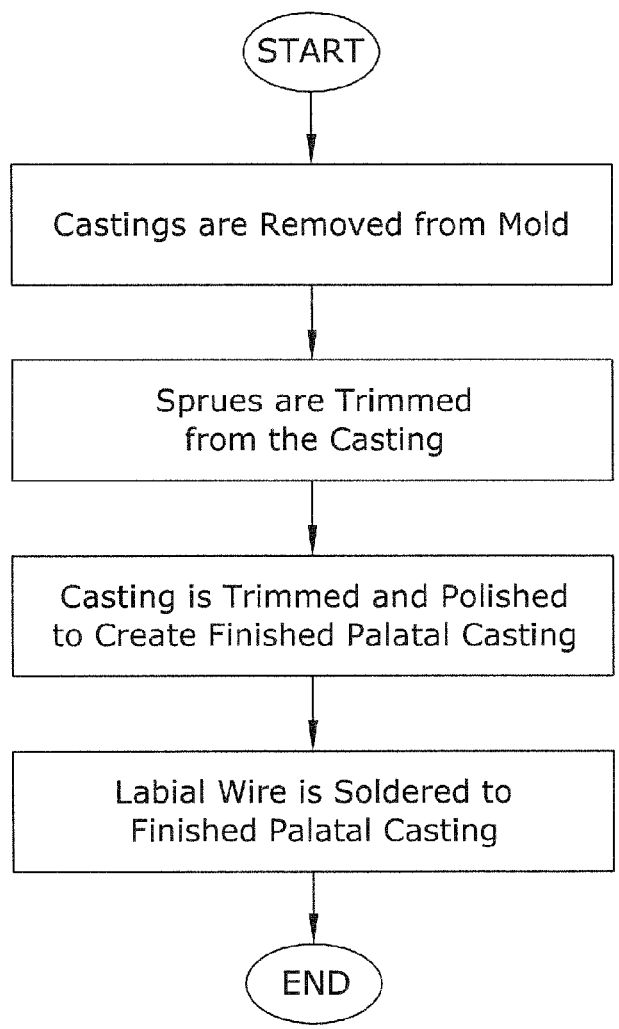
FIG. 13 is a flowchart illustrating the final steps of fabrication of the present invention.

As illustrated in FIG. 13, the casted metal material may then be removed from the shell and sprues may be trimmed away. The casted palatal portion is then trimmed and polished to create a finished cast palatal portion of an orthodontic retainer 10. A labial wire 32 may then be soldered to the finished palatal portion to create the cast orthodontic retainer system 10. Optionally, Adams clasps 36, ball clasps 37 and/or stabilizing wires 38 may additionally be added to the retainer 10 to accommodate specific applications.

Unless otherwise defined, all technical and scientific terms used herein have the same meaning as commonly understood by one of ordinary skill in the art to which this invention belongs. Although methods and materials similar to or equivalent to those described herein can be used in the practice or testing of the present invention, suitable methods and materials are described above. All publications, patent applications, patents, and other references mentioned herein are incorporated by reference in their entirety to the extent allowed by applicable law and regulations. In case of conflict, the present specification, including definitions, will control. The present invention may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

The invention claimed is:

1. A method of fabricating a palatal portion of an orthodontic retainer, comprising:
   providing a blocked out duplicate of a patient's palate and upper teeth;
   providing a sheet of malleable material;
   warming up said sheet of malleable material;
   creating a palatal impression by pressing said warmed up sheet of malleable material against said blocked out duplicate of a patient's palate;
   placing said palatal impression on a sprue tree;
   enclosing said sprue tree and said palatal impression in a container;
   creating a mold by pouring investment material around said sprue tree and said palatal impression within said container and allowing said investment material to dry;
   creating a negative impression of said palatal impression within said mold by heating a hardened shell within a heating device to melt said palatal impression;
   heating a metal material until said metal material is molten, wherein said metal material is comprised of cobalt, chromium and molybdenum;
   inserting said molten metal material into said negative impression of said palatal impression within said mold;
   cooling said mold to form a palatal portion formed from said metal material; and
   removing said palatal portion from said hardened shell, wherein said palatal portion is comprised of a thickness between 0.20 millimeters and 0.30 millimeters.

2. The method of fabricating a palatal portion of an orthodontic retainer of claim 1, wherein said sheet of malleable material is comprised of a sheet of wax.

3. The method of fabricating a palatal portion of an orthodontic retainer of claim 1, wherein said metal material is comprised of a metal alloy.

* * * * *